United States Patent
Dupras et al.

(10) Patent No.: US 12,041,703 B2
(45) Date of Patent: Jul. 16, 2024

(54) METHODS, SYSTEMS AND ASSEMBLIES FOR SUPPLEMENTING THE SPECTRAL CONTENT OF LIGHT WITH NON-VISIBLE LIGHT

(71) Applicant: SOLLUM TECHNOLOGIES INC., Montreal (CA)

(72) Inventors: Gabriel Dupras, Otterburn Park (CA); François Roy-Moisan, Verdun (CA); Alban Derville, Montreal (CA); Louis Brun, Mont-Royal (CA); Jacques Poirier, Huntingdon (CA); Kassim Tremblay, Montreal (CA)

(73) Assignee: SOLLUM TECHNOLOGIES INC., Montreal (CA)

( * ) Notice: Subject to any disclaimer, the term of this patent is extended or adjusted under 35 U.S.C. 154(b) by 153 days.

(21) Appl. No.: 17/629,724

(22) PCT Filed: Jul. 24, 2020

(86) PCT No.: PCT/CA2020/051022
§ 371 (c)(1),
(2) Date: Jan. 24, 2022

(87) PCT Pub. No.: WO2021/012056
PCT Pub. Date: Jan. 28, 2021

(65) Prior Publication Data
US 2022/0272816 A1 Aug. 25, 2022

Related U.S. Application Data

(60) Provisional application No. 62/878,036, filed on Jul. 24, 2019.

(51) Int. Cl.
*H05B 47/155* (2020.01)
*H05B 45/10* (2020.01)
*H05B 45/325* (2020.01)

(52) U.S. Cl.
CPC .......... *H05B 47/155* (2020.01); *H05B 45/10* (2020.01); *H05B 45/325* (2020.01)

(58) Field of Classification Search
CPC .... H05B 47/155; H05B 45/10; H05B 45/325; H05B 47/11; H05B 47/19; Y02P 60/14; A01G 7/045; A61L 2/10
(Continued)

(56) References Cited

U.S. PATENT DOCUMENTS

| 5,142,562 A | 8/1992 | Guichard et al. |
| 2015/0351325 A1 | 12/2015 | Shelor et al. |

(Continued)

FOREIGN PATENT DOCUMENTS

| CN | 209431307 U | 9/2019 |
| EP | 0310477 A1 | 4/1989 |

(Continued)

OTHER PUBLICATIONS

International Search Regort for PCT/CA2020/051022 dated Oct. 1, 2020, 3p.

(Continued)

*Primary Examiner* — Richard Tan
(74) *Attorney, Agent, or Firm* — Crowell & Moring LLP

(57) ABSTRACT

There is provided a supplemental illumination assembly for supplementing a spectral content of an initial illumination originating from an illuminating lamp. The illuminating lamp includes a main controller. The supplemental illumination assembly includes an elongated body; a plurality of supplemental light emitters mounted on the elongated body, each supplemental light emitter being configured to emit light having an emitter spectrum in a non-visible range; and a local controller provided on the elongated body and configured to control the supplemental light emitters, the local controller being in communication with the main (Continued)

controller of the illuminating lamp to receive control signals therefrom.

**19 Claims, 11 Drawing Sheets
(7 of 11 Drawing Sheet(s) Filed in Color)**

(58) Field of Classification Search
USPC .......................................................... 307/157
See application file for complete search history.

(56) References Cited

U.S. PATENT DOCUMENTS

| | | | | |
|---|---|---|---|---|
| 2015/0372240 A1* | 12/2015 | Lub | ........................ | H05B 33/12 |
| | | | | 546/37 |
| 2016/0192598 A1* | 7/2016 | Haggarty | ............... | H05B 47/19 |
| | | | | 315/297 |
| 2018/0007838 A1 | 1/2018 | McCord | | |
| 2018/0014374 A1 | 1/2018 | Rhodes et al. | | |
| 2018/0014375 A1 | 1/2018 | Dupras et al. | | |
| 2022/0046773 A1* | 2/2022 | Dupras | ................. | H05B 47/11 |

FOREIGN PATENT DOCUMENTS

| | | |
|---|---|---|
| WO | WO 2016/154570 A1 | 9/2016 |
| WO | WO 2020/124224 A1 | 6/2020 |

OTHER PUBLICATIONS

Written Opinion for PCT/CA2020/051022 dated Oct. 1, 2020, 3p.
Extended European Search Report for application no. EP 20845057.7 dated Jun. 5, 2023, 10p.

* cited by examiner

METHODS, SYSTEMS AND ASSEMBLIES FOR SUPPLEMENTING THE SPECTRAL CONTENT OF LIGHT WITH NON-VISIBLE LIGHT This application is a National Phase Application of International Application No. PCT/CA2020/051022, filed Jul. 24, 2020, which claims priority to U.S. Provisional Patent Application No. 62/878,036, filed Jul. 24, 2019, the entireties of both of which are hereby incorporated by reference.

TECHNICAL FIELD

The technical field generally relates to lighting and more particularly concerns methods, systems and assemblies for supplementing a spectral content of an initial illumination in an illuminated space.

BACKGROUND

Lamps reproducing the spectrum of natural sunlight or a portion thereof are known in the art. FIG. 1 (PRIOR ART) is an illustration of a multi-channel lighting system with a plurality of light-emitting diodes (LEDs), described in patent application No. US 2018/0014375 (DUPRAS et al.), that reproduces a visible portion of natural sunlight. This lighting system can be used to reproduce at least some of the visible portions of the natural sunlight, as it is illustrated in FIG. 2 (PRIOR ART). There remains a need for methods, systems and assemblies that provide improvements on the spectral contents of light illuminating a space.

SUMMARY

In accordance with one aspect, there is provided a supplemental illumination assembly for supplementing a spectral content of an initial illumination originating from an illuminating lamp, the illuminating lamp including a main controller, the supplemental illumination assembly including:
  an elongated body;
  a plurality of supplemental light emitters mounted on the elongated body, each supplemental light emitter being configured to emit light having an emitter spectrum in a non-visible range; and
  a local controller provided on the elongated body and configured to control the supplemental light emitters, the local controller being in communication with the main controller of the illuminating lamp to receive control signals therefrom.

In some embodiments, said supplemental light emitters include at least one far-red solid-state emitter, the emitter spectrum of each of said at least one far-red solid-state emitter including wavelengths between about 700 nm and about 860 nm.

In some embodiments, said supplemental light emitters include at least one infrared solid-state emitter, the emitter spectrum of each of said at least one infrared solid-state emitter including wavelengths above about 860 nm.

In some embodiments, said supplemental light emitters include at least one ultraviolet (UV) emitter, the emitter spectrum of each of said at least one solid-state emitter including wavelengths between about 10 nm and about 400 nm.

In some embodiments, said supplemental light emitters are light emitting diodes.

In some embodiments, each of said supplemental light emitters is one of a semiconductor light emitting diode, a semiconductor laser diode, a vertical cavity surface emitting laser, an organic light-emitting diode or a polymer light-emitting diode.

In some embodiments, said supplemental light emitters includes a plurality of blocks of light emitting diodes.

In some embodiments, said supplemental light emitters are arranged in a uniform matrix configuration, the plurality of blocks of light emitting diodes including at least one of a block of far-red light emitting diodes, a block of infrared light-emitting diodes and a block of ultraviolet light emitting diodes spaced apart along said elongated body In some embodiments, said supplemental light emitters are arranged in a mixed matrix configuration, each of said plurality of blocks of light emitting diodes including at least two of a block of far-red light emitting diodes, a block of infrared light-emitting diodes and a block of ultraviolet light emitting diodes spaced apart along said elongated body In some embodiments, the local controller operates said supplemental light emitters according to a Pulse Width Modulation scheme.

In some embodiments, the supplemental illumination assembly, further includes a wired connection for connecting said supplemental illumination assembly and the illuminating lamp, said wired connection carrying said control signals and supplying electrical power to the supplemental illumination assembly.

In some embodiments, the supplemental illumination assembly further includes:
  a wireless communication module for wirelessly receiving the control signals from the illuminating lamp; and
  a local power supply provided on the elongated body.

In some embodiments, the elongated body includes an extension bar connectable to the illuminating lamp.

In accordance with another aspect, there is provided a method for supplementing a spectral content of an initial illumination originating from an illuminating lamp, the method including:
  providing a supplemental illumination assembly including one or more supplemental light emitters, each supplemental light emitter being configured to emit light having an emitter spectrum in a non-visible range; and
  combining the light from each of said supplemental light emitters with the initial illumination.

In some embodiments, said one or more supplemental light emitters includes at least one far-red solid-state emitter, the emitter spectrum of each of said at least one far-red solid-state emitter including wavelengths between about 700 nm and about 860 nm.

In some embodiments, said one or more supplemental light emitters includes at least one infrared (IR) solid-state emitter, the emitter spectrum of each of said at least one IR solid-state emitter including wavelengths above about 860 nm.

In some embodiments, said one or more supplemental light emitters includes at least one ultraviolet (UV) emitter, the emitter spectrum of each of said at least one UV solid-state emitter including wavelengths between about 10 nm and about 400 nm.

In some embodiments, the method further includes independently adjusting an intensity level of the light from each of said one or more supplemental emitters.

In some embodiments, the method further includes controlling said one or more supplemental light emitters in view of a target spectrum of the combined light from said supplemental light emitters and said initial illumination.

In accordance with another aspect, there is provided a method for supplementing an initial illumination of a plant growing area, the initial illumination originating from an illuminating lamp, the method including:
- providing a supplemental illumination assembly including one or more supplemental light emitters, each supplemental light emitter being configured to emit non-visible light having an emitter spectrum in a non-visible range; and
- combining the non-visible light with the initial illumination;
- wherein the emitter spectra of said supplemental light emitters is selected to enhance at least one plant growing feature.

In some embodiments, the at least one plant growing feature includes cleaning and disinfecting plants, and the corresponding emitter spectra include wavelength in the UV-C range.

In some embodiments, the at least one plant growing feature includes pollination stimulation, and the corresponding emitter spectra include wavelength in the UV-A and/or UV-B range.

In some embodiments, the at least one plant growing feature includes stimulating plants growth and/or quality, and the corresponding emitter spectra include wavelength in the far-red and/or infrared range.

In some embodiments, the method further includes:
- determining a relative intensity between the emitter spectra of two of said supplemental emitters; and
- controlling said one or more supplemental light emitters to adjust an intensity level of the non-visible light therefrom according to the relative intensity between said two emitter spectra.

In some embodiments, the method further includes:
- determining a relative intensity between an emitter spectrum of one of said supplemental emitters and a spectral band of the initial illumination; and
- controlling said one or more supplemental light emitters to adjust an intensity level of the non-visible light according to the relative intensity between the emitter spectrum of said one of said supplemental emitters and the spectral band of the initial illumination.

In some embodiments, the method further includes independently adjusting an intensity level of the light from each of said one or more supplemental emitters.

In some embodiments, the method further includes controlling said one or more supplemental light emitters in view of a target spectrum of the combined light from said supplemental light emitters and said initial illumination.

In accordance with another aspect, there is provided an extension bar for supplementing a spectral content of an initial illumination originating from an illuminating lamp and irradiating a plant, the illuminating lamp including a main controller, the extension bar including:
- an elongated body;
- one or more supplemental light emitters mounted on the elongated body, each supplemental light emitter being configured to emit non-visible light having an emitter spectrum in a non-visible range; and
- a local controller provided on the elongated body and being in communication with the main controller of the illuminating lamp, the local controller being configured for:
  - determining a relative intensity between two emission spectra; and
  - controlling said one or more supplemental light emitters to adjust an intensity level of the emitter spectrum according to the relative intensity between said two emission spectra.

In some embodiments, each of the two emission spectra is associated with a corresponding one of said one or more supplemental light emitters.

In some embodiments, one of the two emission spectra is associated with a corresponding one of said one or more supplemental light emitter and another one of the two emission spectra is associated with the initial illumination.

In some embodiments, said one or more supplemental light emitters include at least one far-red solid-state emitter, the emitter spectrum of each of said at least one far-red solid-state emitter including wavelengths between about 700 nm and about 860 nm.

In some embodiments, said one or more supplemental light emitters include at least one infrared solid-state emitter, the emitter spectrum of each of said at least one infrared solid-state emitter including wavelengths above about 860 nm.

In some embodiments, said one or more supplemental light emitters include at least one ultraviolet (UV) emitter, the emitter spectrum of each of said at least one solid-state emitter including wavelengths between about 10 nm and about 400 nm.

In some embodiments, said one or more supplemental light emitters are light emitting diodes.

In some embodiments, each of said supplemental light emitters is one of a semiconductor light emitting diode, a semiconductor laser diode, a vertical cavity surface emitting laser, an organic light-emitting diode or a polymer light-emitting diode.

In some embodiments, said one or more supplemental light emitters includes a plurality of blocks of light emitting diodes.

In some embodiments, said one or more supplemental light emitters are arranged in a uniform matrix configuration, the plurality of blocks of light emitting diodes including at least one of: a block of far-red light emitting diodes, a block of infrared light-emitting diodes and a block of ultraviolet light emitting diodes spaced apart along said elongated body.

In some embodiments, said one or more supplemental light emitters are arranged in a mixed matrix configuration, each of said plurality of blocks of light emitting diodes including at least two of: a far-red light emitting diode, an infrared light-emitting diodes and an ultraviolet light emitting diodes spaced apart along said elongated body.

In some embodiments, the local controller operates the one or more light-emitting diodes according to a Pulse Width Modulation scheme.

In some embodiments, the extension bar further includes a wired connection for connecting said extension bar and the illuminating lamp, said wired connection carrying said control signals and supplying electrical power to the supplemental illumination assembly.

In some embodiments, the extension bar further includes:
- a wireless communication module for wirelessly receiving the control signals from the illuminating lamp; and
- a local power supply provided on the elongated body.

In accordance with another aspect, there is provided a modular illumination assembly for irradiating a plant, the modular illumination assembly including:
- a visible illumination module including a main controller, the visible illumination module being configured to emit an initial illumination irradiating a plant, the initial illumination having an initial spectrum in a visible range; and a non-visible illumination module operatively connectable with the visible illumination module, the non-visible illumination module including:

one or more supplemental light emitters, each supplemental light emitter being configured to emit non-visible light having an emitter spectrum in a non-visible range; and a local controller in communication with the main controller of the visible illumination module, the local controller being configured for:

determining a relative intensity between two emission wavelengths; and controlling said one or more supplemental light emitters to emit the non-visible light according to the relative intensity between two emission wavelengths.

In some embodiments, each of the two emission wavelengths is associated with a corresponding one of said one or more supplemental light emitters In some embodiments, one of the two emission wavelengths is associated with a corresponding one of said one or more supplemental light emitter and another one of the two emission wavelengths is associated with the initial illumination.

In some embodiments, said one or more supplemental light emitters include at least one far-red solid-state emitter, the emitter spectrum of each of said at least one far-red solid-state emitter including wavelengths between about 700 nm and about 860 nm.

In some embodiments, said one or more supplemental light emitters include at least one infrared solid-state emitter, the emitter spectrum of each of said at least one infrared solid-state emitter including wavelengths above about 860 nm.

In some embodiments, said supplemental light emitters include at least one ultraviolet (UV) emitter, the emitter spectrum of each of said at least one solid-state emitter including wavelengths between about 10 nm and about 400 nm.

In some embodiments, said one or more supplemental light emitters are light emitting diodes.

In some embodiments, each of said supplemental light emitters is one of a semiconductor light emitting diode, a semiconductor laser diode, a vertical cavity surface emitting laser, an organic light-emitting diode or a polymer light-emitting diode.

In some embodiments, said one or more supplemental light emitters are arranged in a uniform matrix configuration, the plurality of blocks of light emitting diodes including at least one of a block of far-red light emitting diodes, a block of infrared light-emitting diodes and a block of ultraviolet light emitting diodes.

In some embodiments, said one or more supplemental light emitters are arranged in a mixed matrix configuration, each of said plurality of blocks of light emitting diodes including at least two of a block of far-red light emitting diodes, a block of infrared light-emitting diodes and a block of ultraviolet light emitting diodes.

In some embodiments, the local controller operates the one or more light-emitting diodes according to a Pulse Width Modulation scheme.

In some embodiments, the modular illumination assembly further includes a wired connection for connecting said non-visible illumination module and the visible illumination module, said wired connection carrying said control signals and supplying electrical power to the non-visible illumination module.

In some embodiments, the modular illumination assembly further includes:

a wireless communication module for wirelessly receiving the control signals from the visible illumination module; and a local power supply provided on the non-visible illumination module.

In accordance with another aspect, there is provided a method for supplementing a spectral content of an initial illumination in an illuminated space, including providing a supplemental illumination assembly comprising one or more supplemental light emitters, each supplemental light emitter being configured to emit light having an emitter spectrum in a non-visible range and combining the light from each of said supplemental light emitter with the initial illumination.

In some embodiments, the emitter spectrum of at least one of the supplemental light emitters is within the ultraviolet (UV) range.

In some embodiments, the emitter spectrum of at least one of the supplemental light emitters is within the far-red range.

In some embodiments, the emitter spectrum of at least one of the supplemental light emitters is within the infrared (IR) range.

In some embodiments, said one or more supplemental light emitters is a plurality of said supplemental light emitters, and the method further comprises controlling said supplemental light emitters in view of a target spectrum.

In some embodiments, the initial illumination originates from an illuminating lamp provided in said space, to perform said controlling of the supplemental light emitters.

In some embodiments, the method comprises measuring a spectrum of the initial illumination and performing said controlling based on a comparison of said measured spectrum with the target spectrum.

In accordance with another aspect, there is provided a supplemental illumination assembly for supplementing a spectral content of an initial illumination in an illuminated a space, comprising one or more supplemental light emitters, each supplemental light emitter being configured to emit light having an emitter spectrum in a non-visible range. The supplemental illumination assembly may include a combiner combining the light from each of said supplemental light emitter with the initial illumination.

In some embodiments, the supplemental illumination assembly further comprises a controller configured for controlling said supplemental light emitters in view of a target spectrum.

In accordance with another aspect, there is provided a lighting system comprising an illumination lamp for providing an initial illumination in a space; one or more supplemental light emitters, each supplemental light emitter being configured to emit light having an emitter spectrum in a non-visible range; and a combiner combining the light from each of said supplemental light emitter with the initial illumination.

In accordance with another aspect, there is provided a method for supplementing a spectral content of an output illuminating beam to illuminate a space, the output illuminating beam having an illumination spectrum covering a visible portion of a natural light, comprising providing a plurality of solid-state light emitters, each being configured to emit an emitter beam having an individual emitter spectrum; combining the plurality of emitter beams from the plurality of solid-state light emitters into a supplementary output illuminating beam for illumination of the space together with the output illuminating beam, the supplementary output illuminating beam having a supplementary illumination spectrum defined from a combination of the individual emitter spectra of the plurality of emitter beams, the combination of the individual emitter spectra of the plurality of emitter beams covering a non-visible portion of the natural light and excluding the visible portion of the natural light; and controlling the plurality of solid-state light emitters such that the supplementary illumination spectrum is representative of the natural light spectral profile over the non-visible portion.

In accordance with another aspect, there is provided a lighting system for supplementing a spectral content of an output illuminating beam to illuminate a space, the output illuminating beam having an illumination spectrum covering a visible portion of a natural light, comprising a plurality of solid-state light emitters, each being configured to emit an emitter beam having an individual emitter spectrum, the individual spectra of the solid-state light emitters collectively covering a non-visible portion of the natural light spectral profile and excluding the visible portion of the natural light a beam combining assembly configured to combine the emitter beams emitted by the plurality of solid-state light emitters into a supplementary output illuminating beam for illumination of the space together with the output illuminating beam, the supplementary output illuminating beam having a supplementary illumination spectrum defined from a combination of the individual emitter spectra of the plurality of emitter beams; and a controller configured for controlling the plurality of solid-state light emitters such that the supplementary illumination spectrum is representative of the natural light spectral profile over the non-visible portion.

In accordance with another aspect, there is provided a method for supplementing a spectral content of an output illuminating beam to illuminate a space according to a target illumination spectrum, the output illuminating beam having an illumination spectrum representative of a natural light, comprising determining a reference illumination spectrum associated with the output illuminating beam determining a spectral deviation between the reference illumination spectrum and the target illumination spectrum; providing a plurality of solid-state light emitters, each being configured to emit an emitter beam having an individual emitter spectrum; combining the plurality of emitter beams from the plurality of solid-state light emitters into a supplementary output illuminating beam for illumination of the space together with the output illuminating beam, the supplementary output illuminating beam having a supplementary illumination spectrum defined from a combination of the individual emitter spectra of the plurality of emitter beams, the combination of the individual emitter spectra of the plurality of emitter beams covering a non-visible portion of the natural light; and controlling the plurality of solid-state light emitters to adjust the supplementary illumination spectrum of the supplementary beam illuminating beam to match the spectral deviation and illuminate the space according to the target illumination spectrum.

In accordance with another aspect, there is provided a lighting system for supplementing a spectral content of an output illuminating beam to illuminate a space according to a target illumination spectrum, the output illuminating beam having an illumination spectrum representative of a natural light, the lighting system comprising a plurality of solid-state light emitters, each solid-state light emitter being configured to emit an emitter beam according to an individual emitter spectrum; a beam combining assembly configured to combine the emitter beams emitted by the plurality of solid-state light emitters into a supplementary output illuminating beam for illumination of the space together with the output illuminating beam, the supplementary output illuminating beam having a supplementary illumination spectrum defined from a combination of the individual emitter spectra of the plurality of emitter beams, the combination of the individual emitter spectra of the plurality of emitter beams covering a non-visible portion of the natural light; and a control and processing unit operatively coupled to the plurality of solid-state light emitters, the control and processing unit being configured to determine a reference illumination spectrum associated with the output illuminating beam; determine a spectral deviation between the reference illumination spectrum and the target illumination spectrum; and control the plurality of solid-state light emitters to adjust the supplementary illumination spectrum of the supplementary beam illuminating beam to match the spectral deviation and illuminate the space according to the target illumination spectrum.

The provided methods, systems and assemblies may be used to increase, supplement and/or complement the range of wavelengths emitted by a light source, such as, for example, a conventional visible light source. In some implementations, the systems and assemblies can be provided as an extension bar that can be mounted or added to an existing white light source. The combination of a conventional visible light source with the provided systems and assemblies can allow supplementing the spectral content of the conventional visible light source with wavelengths in the UV portion and/or the IR portion of the electromagnetic spectrum, thereby supplementing the spectral content of the conventional visible light source.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
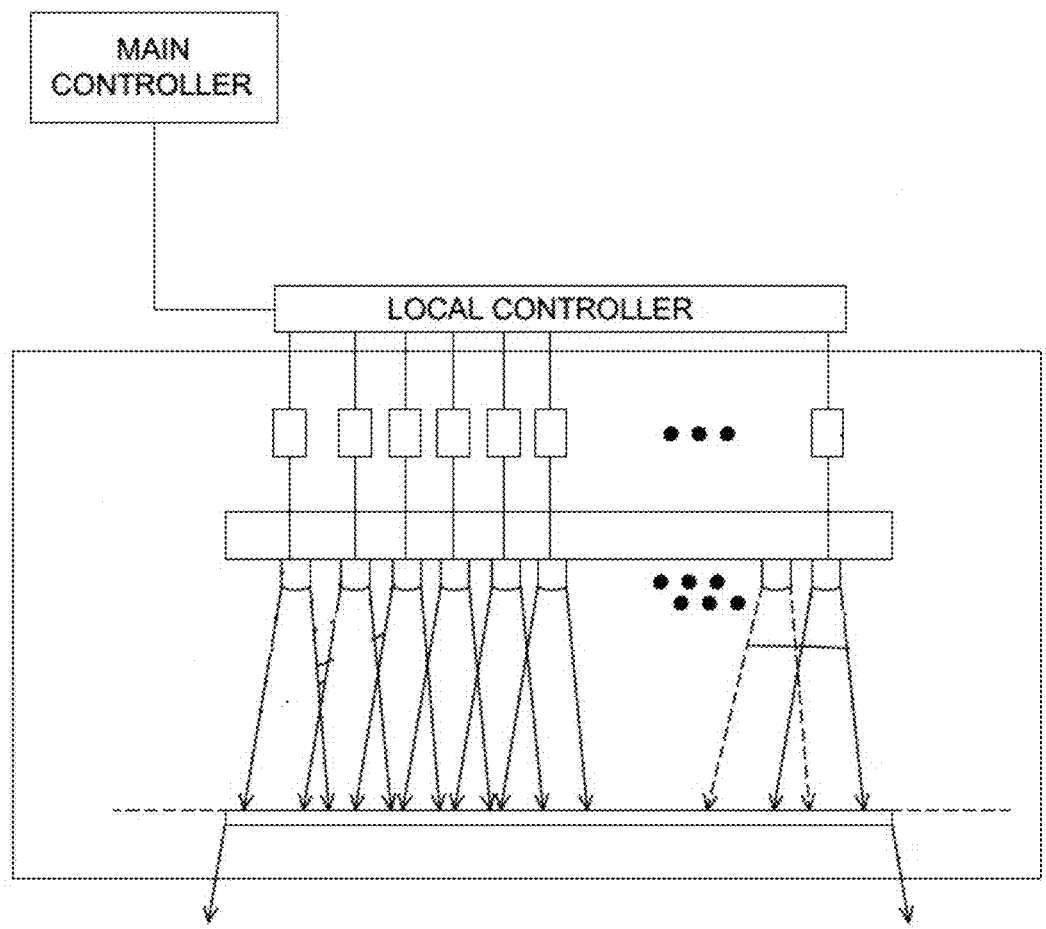
FIG. 1 (PRIOR ART) is a schematic representation of a LED lighting system from prior art.

In the following description, similar features in the drawings have been given similar reference numerals, and, to not unduly encumber the figures, some elements may not be indicated on some figures if they were already identified in one or more preceding figures. It should also be understood herein that the elements of the drawings are not necessarily depicted to scale, since emphasis is placed upon clearly illustrating the elements and structures of the present embodiments. Furthermore, positional descriptors indicating the location and/or orientation of one element with respect to another element are used herein for ease and clarity of description. Unless otherwise indicated, these positional descriptors should be taken in the context of the figures and should not be considered limiting. More particularly, it will be understood that such spatially relative terms are intended to encompass different orientations in the use or operation of the present embodiments, in addition to the orientations exemplified in the figures. The terms "a", "an" and "one" are defined herein to mean "at least one", that is, these terms do not exclude a plural number of elements, unless stated otherwise. It should also be noted that terms such as "substantially", "generally" and "about", that modify a value, condition or characteristic of a feature of an exemplary embodiment, should be understood to mean that the value, condition or characteristic is defined within tolerances that are acceptable for the proper operation of this exemplary embodiment for its intended application.

In the present description, the terms "connected", "coupled", and variants and derivatives thereof, refer to any connection or coupling, either direct or indirect, between two or more elements. The connection or coupling between the elements may be mechanical, physical, optical, operational, electrical, wireless, or a combination thereof.

In the present description, the terms "light" and "optical", and any variants and derivatives thereof, are intended to refer to electromagnetic radiation in any appropriate region of the electromagnetic spectrum and are not limited to visible light, unless otherwise specified. For example, in one embodiment, the terms "light" and "optical" may encompass electromagnetic radiation with a wavelength ranging from about 200 to about 2500 nm. More particularly, the expressions may encompass electromagnetic radiation(s) with a wavelength from about 250 nm to about 1 mm. Although embodiments of the present techniques can be useful in ultraviolet (UV) range, far-red range, and infrared (IR) range applications, other embodiments could additionally or alternatively operate in other regions of the electromagnetic spectrum. It is to be noted that, in the context of the present description, the UV range extends sub-200 nm to approximately 400 nm, the far-red range extends form approximately 700 nm to approximately 860 nm and the IR range extends from approximately 860 nm and above (e.g., approximately 1 mm).

In the context of the current disclosure, the expression "natural light" and similar expressions and variants thereof may refer to the light emitted by the sun or a lamp reproducing a target natural light, the target natural light resembling the sunlight, and more particularly the spectral profile of the sun. One skilled in the art will understand that the natural light has similar spectral characteristics as light of the sun reaching the earth. As such, the natural light has a natural spectral profile that is defined as being the variation in light intensity as a function of wavelengths. As known to those skilled in the art, the spectral profile of light from the sun can vary depending on several factors such as the time of the day, the period of the year, the geographic location and several other factors.

In the present description, the terms "initial illumination" and "output illuminating light" are intended to refer to any light used for illuminating a space and whose illumination spectrum can be supplemented, enhanced, optimized, improved, supported or completed according to the techniques, methods, systems and/or assemblies that will be described in the current disclosure. These terms could be used interchangeably in the current description. Depending on the application, the initial illumination or the output illuminating light can be produced by artificial light source(s), natural light source(s), or a combination thereof.

In the present description, the term "illumination spectrum" or "supplementary illumination spectrum" are used to broadly refer to the spectral distribution of a predetermined illumination type. For instance, the illumination spectrum is associated with the output illuminating beam, whereas the supplementary illumination spectrum is associated with the supplementary output illuminating beam. As known in the art, a spectrum can represent the distribution of power radiated per unit area and per unit wavelength or frequency over a spectral region of the electromagnetic spectrum.

In the present description, the term "space" is meant to encompass any region, scene, area, surface, environment, target, object, feature or information of interest which can be illuminated according to according to the present techniques. In some embodiments, the techniques herein described may be used in the context of supplementing an initial illumination of a plant growing area.

The term "target illumination spectrum" is intended to refer herein to any desired or required illumination spectrum to be achieved according to the present technique as result of supplementing the initial illumination (sometimes referred to as the "output illuminating beam") with the supplementary output illuminating beam emitted by the supplemental illumination assembly, as it will be described in greater detail below. In the present techniques, the target illumination spectrum can be obtained by adjusting the illumination spectrum of the light emitters to match a difference between the illumination spectrum of the initial illumination and the target illumination spectrum to be achieved. In some implementations, the target illumination spectrum can be selected to reproduce natural light, such as sunlight, under certain geographical (e.g., latitude, longitude, and altitude), temporal (e.g., with respect to the time of day or the time of year), meteorological (e.g., sunny, rainy, cloudy, overcast, foggy, snowy, stormy, and smoggy) conditions. Particularly, the present techniques can use the output supplementary illuminating beam to fill one or more gaps in the illumination spectrum of the initial illumination to obtain a target illumination spectrum that is closer to desired lighting conditions.

Figure 2:
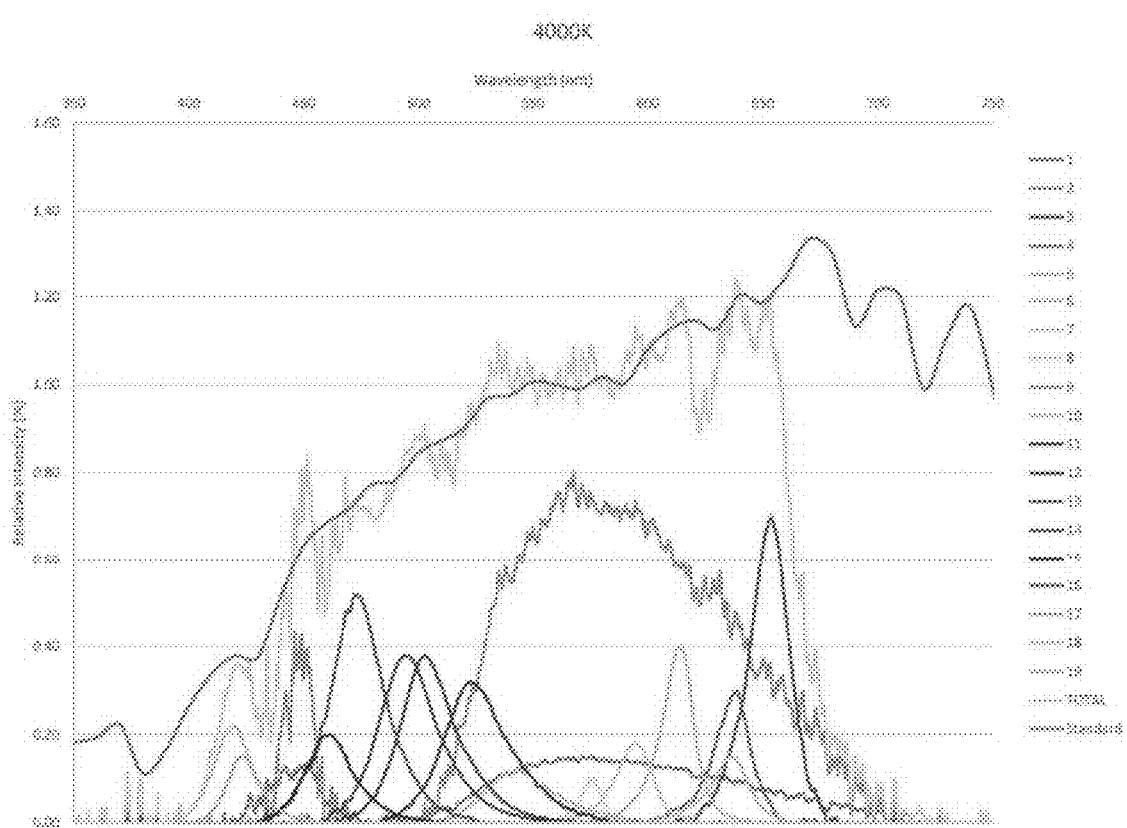
FIG. 2 (PRIOR ART) is a graph showing the individual spectral profile of each light emitter included in the system of FIG. 1.

FIG. 1 (PRIOR ART) is representative of a LED lighting system of prior art and FIG. 2 (PRIOR ART) depicts the spectral profile of the light emitted by each individual light emitter of the lighting system of FIG. 1. As it can be seen, the spectral profiles of 19 LEDs are combined to obtain the visible portion of the natural light. In FIG. 2 (PRIOR ART), the relative intensities of the LEDs are configured to provide natural light at a color temperature of about 4000 K. The combined spectral profiles illustrated in FIG. 2 (PRIOR ART) span a wavelength range extending between about 400 nm and 700 nm The present description generally relates to methods, systems and assemblies for supplementing the spectral content of an initial illumination with a supplemental illumination assembly that emits UV and/or IR light, i.e., non-visible light. The UV and/or IR portions of the electromagnetic spectrum can be useful in many applications, when used in conjunction with the visible portions of natural sunlight or artificial sunlight.

In US 2018/0014375, the ultraviolet and infrared portions of the electromagnetic spectrum are excluded, as these wavelengths are considered to be undesirable for the targeted applications. In other words, the system disclosed in US 2018/0014375A1 generates a beam having a spectral profile representative of the natural sunlight over the visible spectrum only and exclude the undesirable wavelengths, being the infrared and ultraviolet components in this case.

There are other examples of circumstance where UV and/or IR components are missing from the initial illumination of a space. According to one such example, non-visible spectral components of light from the sun can be blocked by glass or other semi-transparent interface through which sunlight enters to illuminate room or other space.

Depending on the targeted application(s), the methods, systems and assemblies provided herein can be adjusted to emit certain wavelengths and exclude others. UV light ranging from approximately 10 nm to approximately 400 nm can be used in many fields such as, for example and without being limitative, medical field, sanitary applications, chemistry, therapy and many others. As such, the techniques provided in the current disclosure could be used to generate a dose of UV light that may be required over a relatively short time period, in addition to conventional lighting applications. One potential application is in the field of light therapy, in which the wavelengths extending form about 300 nm to about 320 nm can be particularly useful. In the case of the far red and IR ranges, which range from about 700 nm and above (e.g., 1 mm) the techniques disclosed in the current description can be used for applications in night vision, thermography, heating, medical treatment and many others.

The methods, systems and assemblies that will now be described with reference to the Figures allow supplementing the spectral content of an initial illumination originating from an illuminating lamp, either by "doses" (i.e., intermittent illumination regime) or with constant radiation (i.e., constant illumination regime).

Method for supplementing a spectral content of an initial illumination originating from an illuminating lamp Broadly described, the description relates to a method for supplementing a spectral content of an initial illumination for supplementing a spectral content of an initial illumination originating from an illuminating lamp. This method includes providing a supplemental illumination assembly including one or more supplemental light emitters, wherein each supplemental light emitter is configured to emit light having an emitter spectrum in a non-visible range of the electromagnetic spectrum. In some embodiments, the supplemental light assembly includes a plurality of supplemental light emitters. It is to be noted that in the context of the current disclosure, such light emitters are going to be referred to as "non-visible light emitters" and the expression "emitter spectrum in a non-visible range of the electromagnetic spectrum" could be interchangeably used with the expression "non-visible light". As one will note, the non-visible light emitters can emit UV or IR light, i.e., light having a wavelength that cannot generally be seen with a naked eye. The method also includes combining the light from each of the supplemental light emitters with the initial illumination.

In some embodiments, the emitter spectrum of one or more of the supplemental light emitters is within the UV range. This can be achieved with one or more LEDs emitting in the UV portion of the electromagnetic spectrum. The emitter spectrum of one or more of the supplemental light emitters can also be within the far-red range, which can be achieved with one or more LEDs emitting in the far-red portion of the electromagnetic spectrum. The emitter spectrum of one or more of the supplemental light emitters can be within the IR range. This can be achieved with one or more LEDs emitting in the IR portion of the electromagnetic spectrum. Any combination of UV, far-red and IR light emitters may be used.

In some embodiments, the supplemental light emitters comprise at least one far-red solid-state emitter. The emitter spectrum of each of the at least one far-red solid-state emitter may comprise wavelengths between about 700 nm and about 860 nm. The supplemental light emitters may also comprise at least one infrared solid-state emitter. The emitter spectrum of each of the IR solid-state emitter may comprise wavelengths above about 860 nm. The supplemental light emitters may comprise at least one ultraviolet (UV) emitter. The emitter spectrum of the UV solid-state emitter may comprise wavelengths between about 10 nm and about 400 nm.

It will be noted that the emitter spectrum of each of the supplemental light emitters can be in the same spectral region of the electromagnetic spectrum, and so can extend over the UV region only, the far-red region only or the IR region only. Alternatively, the supplemental illumination assembly can include a combination of LEDs emitting in the UV, the far-red and/or the IR range portions of the electromagnetic spectrum, so as to supplement the spectral content of the initial illumination in different spectral regions, e.g., at least two of the UV, far-red and IR portions. In this embodiment, the provided supplemental illumination assembly can be an extension bar onto which are mounted the supplemental light emitters. The extension bar configuration will be described in greater detail below.

When the supplemental light assembly includes a plurality of supplemental light emitters, the methods can include controlling the supplemental light emitters. This step of controlling the supplemental light emitters can be made in view of a target spectrum, as it will be described in greater detail below. In some embodiments, the initial illumination originates from an illuminating lamp provided in the space being illuminated, in order to perform the control of the supplemental light emitters.

The method can also include a step of measuring a spectrum of the initial illumination and performing the control of the supplemental light emitters based on a comparison of the measured spectrum with the target spectrum.

In some embodiments, the method may further include independently adjusting an intensity level of the light from each of the supplemental emitters.

Figure 3:
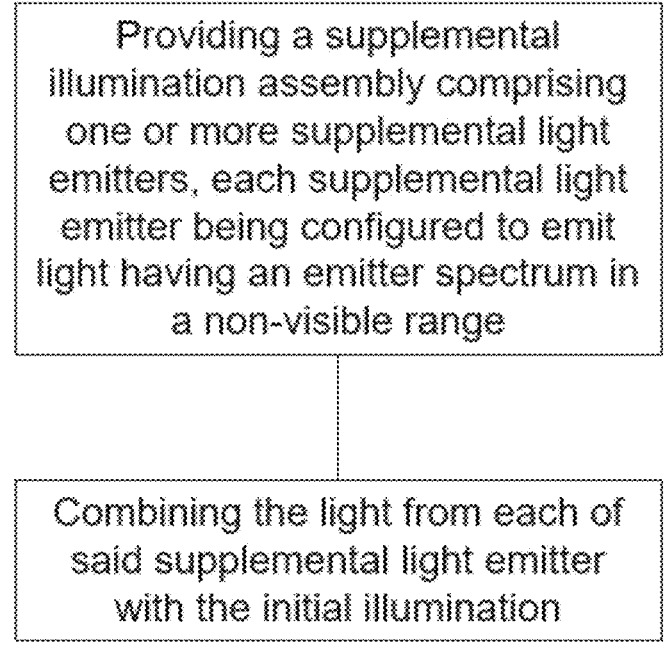
FIG. 3 is a flow diagram of a method for supplementing a spectral content of an output illuminating beam to illuminate a space, the output illuminating beam having an illumination spectrum covering a visible portion of a natural light, in accordance with a possible embodiment.

Now turning to FIG. 3, there is illustrated an embodiment of a method for supplementing a spectral content of an initial illumination originating from an illuminating lamp. In this embodiment, the output illuminating beam has an illumination spectrum covering a visible portion of a natural light.

The method according to this embodiment includes a step of providing a plurality of solid-state light emitters, each being configured to emit an emitter beam having an individual emitter spectrum. In some embodiments, the plurality of solid-state light emitters is embodied by a set of LEDs. The set of LEDs can include several LEDs having the same spectral profile (i.e., emitting an emitter beam having a substantially similar individual emitter spectrum), which can be used to reach a predetermined power level at a given wavelength.

The method further includes a step of combining the plurality of emitter beams from the plurality of solid-state light emitters into a supplementary output illuminating beam. The supplementary output illuminating beam has a supplementary illumination spectrum defined from a combination of the individual emitter spectra of the plurality of emitter beams. The resulting combination of the individual emitter spectra of emitter beams covers a non-visible portion of the natural light, e.g., UV, far-red and/or IR, and excludes the visible portion of the natural light. One of the uses of the resulting supplementary output is to illuminate the space together with the output illuminating beam, which results in illuminating the space with a light having a spectral profile including non-visible and visible light. It will be noted that the combination could be achieved using optical elements, such as, for example and without being limitative, lenses or diffuser. The combination could also be the result of the positioning of the supplemental light emitters and/or the illuminating lamp.

After the steps of providing the solid-state light emitters and combining the emitter beams, the method may include controlling or driving the solid-state light emitters, so that the supplementary illumination spectrum is representative of the natural light spectral profile over the non-visible portion. This step allows controlling the intensity of certain wavelengths and provides the method with sufficient flexibility to be applicable to a broad variety of potential applications.

Table 1 presents an example of non-visible ranges and their coverage by different supplemental light emitters. The first column presents the contemplated range (UV, far-red and IR) and the right column presents which the emitter spectrum of a broad variety of supplemental light emitters that could potentially be used to cover the non-visible ranges.

For the UV range, three groups are presented in the example of Table 1: UV-C, UV-B and UV-A. As mentioned, each line of the second column illustrates a spectral range that can be covered by one of the supplemental light emitters. For instance, in the case of UV-C, one LED can be used to emit light in the spectral window below 200 nm, another in the 200 to 220 nm region, another in the 220 to 240 nm and another in the 240 to 260 nm. Of course, more than one LED could be used to reach a predetermined intensity, that is dependent on the targeted application. The same goes for the far-red range, extending from approximately 700 nm to approximately 860 nm and the IR range, extending from about 860 nm and above.

TABLE 1

| Emitter spectrum of supplemental light emitters | |
|---|---|
| Range | Wavelengths [nm] |
| UV-C | (. . .) - 200 |
|  | 200 - 220 |
|  | 220 - 240 |
|  | 240 - 260 |
| UV-B | 260 - 280 |
|  | 280 - 300 |
|  | 300 - 320 |
| UV-A | 320 - 340 |
|  | 340 - 360 |
|  | 360 - 380 |
|  | 380 - 400 |
| Far-red | 700 - 720 |
|  | 720 - 740 |
|  | 760 - 780 |
|  | 780 - 800 |
|  | 800 - 820 |
|  | 820 - 840 |
|  | 840 - 860 |
| IR | 860 - 880 |
|  | 880 - (. . .) |

As it has been briefly mentioned, beyond supplementing the spectral content of the output illuminating beam, the method can also be adapted to supplement the spectral content of the output illuminating beam to illuminate the space according to a target illumination spectrum. In these implementations, the output illuminating beam has an illumination spectrum representative of the natural light.

This method may include one or more of the steps which have been previously described with additional steps.

Turning to these additional steps, the method of supplementing the spectral content of the output illuminating beam according to the target illumination spectrum can include determining a reference illumination spectrum associated with the output illuminating beam. After the determination or identification of the reference illumination spectrum, a step of determining a spectral deviation between the reference illumination spectrum and the target illumination spectrum can be performed.

Based on these steps, the step of providing the solid-state light emitters can be carried out. As it has been previously described, each solid-state light emitter is configured to emit an emitter beam having an individual emitter spectrum. This step can be followed with the step of combining the emitter beams from the solid-state light emitters into the supplementary output illuminating beam for illumination of the space together with the output illuminating beam. Again, the supplementary output illuminating beam has a supplementary illumination spectrum defined from the combination of the individual emitter spectra of the plurality of emitter beams and the combination of the individual emitter spectra of the plurality of emitter beams covers a non-visible portion of the natural light. The same control of the light emitters can be achieved to adjust the supplementary illumination spectrum of the supplementary beam illuminating beam to match the spectral deviation and illuminate the space according to the target illumination spectrum.

Supplemental Illumination Assembly

The present description also relates to systems and assemblies for generating non-visible light for supplementing a spectral content of an initial illumination originating from an illuminating lamp including a main controller or a visible natural light spectrum, which may be created by a multi-led illumination source (i.e., artificial source) or the sun.

Figure 4A:
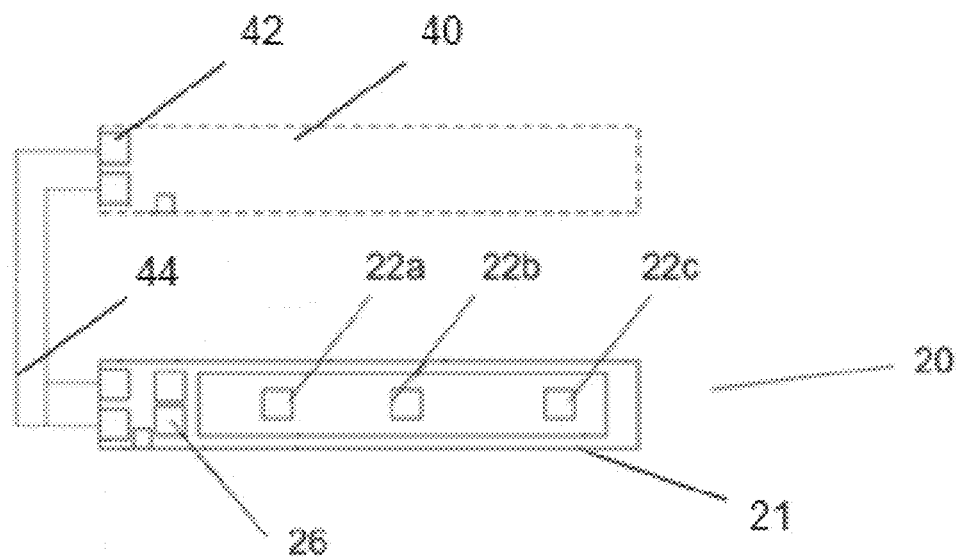
FIG. 4A illustrates a supplemental illumination assembly for supplementing a spectral content of an initial illumination originating from an illuminating lamp, in accordance with one embodiment.

Now turning to FIG. 4A, a supplemental illumination assembly 20 is shown. As illustrated, the illuminating lamp 40 comprises a main controller 42.

The supplemental illumination assembly 20 includes an elongated body 21. The elongated body 21 is sized and configured to support the other components of the supplemental illumination assembly 20.

The supplemental illumination assembly 20 includes one or more supplemental light emitters 22a,b,c. Each supplemental light emitter is configured to emit light having an emitter spectrum in a non-visible range. The non-visible energy flux is controlled with a multi-channels' driver. More particularly, the current on each channel may be controlled with a Pulse Width Modulation (PWM) scheme, as it will be described in greater detail below. The supplemental light emitters 22a,b,c are typically solid-state light emitters and in some embodiments LEDs. In the present description, the term "solid-state light emitter" refers to any light-emitting device that converts electrical energy into electromagnetic radiation through the recombination of electronic carriers (i.e., electrons and holes) in a light emitting layer or region. The emitting layer or region can include, but is not limited to, silicon, silicon carbide, gallium nitride and/or other semiconductor materials, and may or may not include a substrate such as a sapphire, silicon, silicon carbide and/or other microelectronic substrates. The solid-state light emitters can include both inorganic and organic light emitters, many of which are known to the skilled person and need not be described in detail herein. Non-limiting examples of types of solid-state light emitters include semiconductor LEDs, semiconductor laser diodes, vertical cavity surface emitting lasers (VCSELs), other semiconductor light emitting devices or lamps, organic light-emitting diodes (OLEDs), and polymer light-emitting diode (PLEDs).

The supplemental light emitters 22a,b,c can be provided under the form of a mixed matrix including LEDs emitting at different wavelengths, or could be arranged in substantially uniform matrix including LEDs emitting at the same wavelengths or in the same range (i.e., UV, far-red or IR portions of the electromagnetic spectrum). The system can include one or more matrices of LEDs. In the mixed matrix configuration, each of block of light emitting diodes comprises at least two of a block of far-red light emitting diodes, a block of infrared light-emitting diodes and a block of ultraviolet light emitting diodes spaced apart along said elongated body. In the uniform matrix configuration, the blocks of light emitting diodes comprise at least one of a block of far-red light emitting diodes, a block of infrared light-emitting diodes and a block of ultraviolet light emitting diodes spaced apart along said elongated body The supplemental illumination assembly 20 may optionally include a combiner combining the light from each of said supplemental light emitter with the initial illumination. The combiner may be configured to combine the light emitted by the plurality of the supplemental light emitters with the initial illumination to illuminate the space.

The supplemental illumination assembly 20 also includes a local controller 26 provided on the elongated body 21, for controlling the supplemental light emitters. The supplemental light emitters can be controlled through different processes. The local controller 26 is in communication with the main controller 42 of the illuminating lamp 40. The main controller 42 may be operatively connected to the local controller 26 of the supplemental illumination assembly 20. The main controller 42 generates a control signal that may be sent to the local controller 26. In this embodiment, the main controller 42 is provided on the initial illumination source (i.e., the illuminating lamp 40), which can be for example and without being limitative a visible light source, whereas the local controller 26 is provided on the supplemental illumination assembly 20. It is to be noted that the control signal can be sent from the visible light source to the supplemental light illumination assembly through a wire 44, for example and without being limitative, a conductor. In these embodiments, the power input can be provided on the initial illumination assembly. In this embodiment, the initial illumination source is operatively connected to the supplemental illumination assembly 20 and is configured to power the same. At least one of the electric current or voltage applied to the supplemental illumination source can be controlled. In one implementation, the initial illumination source (or a component thereof) can be connected to the supplemental illumination source (or a component thereof) with one or more conductors that can be provided on the same printed circuit board (PCB). In one example a communication cable (e.g., I2C) can be provided between the initial illumination source and the supplemental illumination assembly 20.

In another embodiments, a communication signal is provided by the initial illumination source, i.e., the illuminating lamp 40. The communication can be established between the microcontroller and a PWM generator. The microcontroller can be, for example and without being limitative, located on the initial illumination source, and the PWM generator can be, for example and without being limitative, located on the supplemental illumination assembly 20. The PWM generator can control the LED controller through a different communication protocol, such as, for example, I2C. The PWM generator can be provided as a chip and is configured to transform a signal generated by the I2C into multi-channels PWM signals (through independent channels). In these embodiments, the electrical power is directly provided on the supplemental illumination assembly 20. The I2C signal includes information of each PWM signal and is associated to respective supplemental illumination assembly channels. The I2C signal can originate, i.e., can be an output of the microcontroller located on the initial illumination source.

In some embodiments, the supplemental illumination assembly 20 can have its own power supply, i.e., the supplemental illumination assembly 20 is not powered by the initial illumination source. In these embodiments, the supplemental illumination assembly 20 is said to be in a "stand alone" mode.

In another embodiments, the control signal may be provided through a communication signal like $I^2C$, RS232, RS487 or others. In this embodiment, the control signal is sent to a LED driver through a communication cable. The LED driver can be provided on the supplemental illumination assembly 20. The control signal may be sent through a communication cable to the local controller 26 or the driver located on the supplemental illumination assembly 20. In these embodiments, power input (e.g., a DC connector) is provided directly on the supplemental illumination assembly 20.

In some embodiments, each of the supplemental light emitters 22a,b,c are individually driven by respective drivers which may be scaled to an nth number of drivers for an nth number of supplemental light emitters. In some embodiments, the supplemental light emitters 22a,b,c are solid-state light emitters such as a LED. As it is known by one skilled in the art, LED generates or outputs light when a current is driven across a p-n junction in the semiconductor diode of the LED. The intensity of the light generated by the LED is thus correlated to the amount of current driven through the diode. In one variant, the local controller 26 controls the solid-state emitters according to the PWM briefly introduced above, a known method for controlling the current driven through a LED to achieve desired intensity and/or color mixing. A PWM scheme alternately pulses the LED to a full current "ON" state followed by a zero current "OFF" state. Depending on the command that is given, by controlling the variation of the duty cycle (0-100%), the average luminous power emitted by the LED proportionally increases or decreases. The intensity and the temperature of LED may thus be controlled by the PWM signals issued to the plurality of emitter drivers by the controller. The intensities of the individual spectrum of the light sub-beams emitted by each supplemental light emitter, e.g., LEDs, may be dependent on different working temperatures and different PWM values. Moreover, the local controller 26 may be configured to control the current driven through the supplemental light emitters 22a,b,c using one or more control schemes. For example, to maintain the total lumen output of the lighting system during a dimming function of the supplemental illumination assembly 20, the local controller 26 may regulate the electric current to the supplemental light emitters 22a,b,c using built-in mathematical equations and solid-state light emitter parameter database (not shown) containing information such as LED efficacy, intensity-temperature relations, color shift-temperature relations, the eight CCT quadrangles, and the like, to individually and proportionally control the intensities of the supplemental light emitters. In operation, signals are sent to the drivers from the local controller 26. Each driver then sends its own PWM current pulse to its associated supplemental light emitters. The luminous intensity of the supplementary output illuminating light may be individually adjusted by independently applying particular drive currents to the respective supplemental light emitters 22a,b,c according to the control signals from the local controller 26. The local controller 26 is able to individually control the driving signals from each driver to a respective supplemental light emitter so that the resulting combined spectral profile of the supplemental output illuminating beam is includes the nonvisible portions of the natural light. In some embodiments, the frequencies of the PWM signal may also be adjustable in the ranges between 100 Hz to 10 kHz for implementing lighting functions, such as, for example and without being limitative dimming. A high PWM frequency may be utilized (e.g., between 150 Hz and 1 KHz) such that the on and off flickering of the supplemental light emitters 22a,b,c is generally not perceptible to the naked eye.

In some implementations, the supplemental illumination assembly 20 is a lighting system for supplementing a spectral content of an output illuminating beam to illuminate a space. The output illuminating beam has an illumination spectrum covering a visible portion of a natural light. The lighting system includes a plurality of solid-state light emitters, each being configured to emit an emitter beam having an individual emitter spectrum. The individual spectra of the solid-state light emitters collectively cover a non-visible portion of the natural light spectral profile and exclude the visible portion of the natural light. The lighting system includes a beam combining assembly configured to combine the emitter beams emitted by the plurality of solid-state light emitters into a supplementary output illuminating beam for illumination of the space together with the output illuminating beam. The supplementary output illuminating beam has a supplementary illumination spectrum defined from a combination of the individual emitter spectra of the plurality of emitter beams. The lighting system also includes a controller configured for controlling the plurality of solid-state light emitters such that the supplementary illumination spectrum is representative of the natural light spectral profile over the nonvisible portion.

In some embodiments, the local controller 26 may be further configured for controlling the supplemental light emitters 22a,b,c in view of a target spectrum.

The present description also relates to a lighting system. The lighting system includes the illumination lamp 40 for providing the initial illumination in the space, similar to the one which has been previously described. The lighting system also includes one or more supplemental light emitters 22a,b,c, each supplemental light emitter being configured to emit light having an emitter spectrum in a non-visible range. The supplemental light emitters 22a,b,c are similar to the ones which have been previously described. The lighting system may further include a combiner for combining the light from each of said supplemental light emitter with the initial illumination, as it has been previously presented. In these embodiments, the supplemental illumination assembly 20 can be a lighting system that includes a plurality of solid-state light emitters, and each solid-state light emitter is configured to emit an emitter beam according to an individual emitter spectrum. The lighting system can also include a beam combining assembly configured to combine the emitter beams emitted by the plurality of solid-state light emitters into a supplementary output illuminating beam for illumination of the space together with the output illuminating beam. The supplementary output illuminating beam has a supplementary illumination spectrum defined from a combination of the individual emitter spectra of the plurality of emitter beams, and the combination of the individual emitter spectra of the plurality of emitter beams covers a non-visible portion of the natural light. The lighting system also include a controller operatively coupled to the plurality of solid-state light emitters. The controller is configured to determine a reference illumination spectrum associated with the output illuminating beam, determine a spectral deviation between the reference illumination spectrum and the target illumination spectrum and control the solid-state light emitters to adjust the supplementary illumination spectrum of the supplementary beam illuminating beam to match the spectral deviation and illuminate the space according to the target illumination spectrum.

In some embodiments, the supplemental illumination assembly 20 or the lighting system can be provided as an extension bar ("bar configuration"). In these embodiments, the system or assembly includes an elongated body 21 onto which are mounted the supplemental light emitters 22a,b,c emitting light in a non-visible range. The extension bar can include LEDs having a spectrum ranging between about 100 nm to about 400 nm for the UV range and about 700 nm to about 1500 nm for far-red and IR range. When provided in the bar configuration, the supplemental illumination assembly 20 or the lighting system can form module(s) that can be added to an existing lighting system, lamp or similar assembly. A plurality of extension bars can be connected, either in parallel or in series with one another and with respect to the initial illumination.

In some embodiments, the systems and assemblies can be combined with a sensor to collect information relative to the initial illumination and monitoring the same.

In accordance with another aspect of the present description, there is provided a non-transitory computer readable storage medium having stored thereon computer executable instructions that, when executed by a processor, cause the processor to perform the methods that have been previously described. The non-transitory computer storage medium can be integrated to the systems or assemblies that have been described in the present description. The non-transitory computer storage medium could otherwise be operatively connected with the systems or assemblies. In the present description, the terms "computer readable storage medium" and "computer readable memory" are intended to refer to a non-transitory and tangible computer product that can store and communicate executable instructions for the implementation of various steps of the method disclosed herein. The computer readable memory can be any computer data storage device or assembly of such devices, including random-access memory (RAM), dynamic RAM, read-only memory (ROM), magnetic storage devices such as hard disk drives, solid state drives, floppy disks and magnetic tape, optical storage devices such as compact discs (CDs or CDROMs), digital video discs (DVD) and Blu-Ray™ discs; flash drive memory, and/or other non-transitory memory technologies. A plurality of such storage devices may be provided, as can be understood by those skilled in the art. The computer readable memory may be associated with, coupled to, or included in a computer or processor configured to execute instructions contained in a computer program stored in the computer readable memory and relating to various functions associated with the computer.

The systems and assemblies herein described allow different possible combinations. For example, and without being limitative, the systems and assemblies may be UV only, far-red only or IR only. In other embodiments, the systems and assemblies can emit a combination of UV and IR light, UV and far-red light, far-red and IR light, UV, far-red and IR light and any other possible combinations of those three regions of the electromagnetic spectrum. In the context of experimental conditions, this feature could be useful to add a predetermined spectral component to a pre-existing light source, i.e., complementing the light emitted by the source with desired/selected non-visible wavelength. The systems and assemblies could further be used to supplement a natural light spectrum that already contains a certain quantity of non-visible wavelengths, and so can be used to increase the intensity of some wavelengths of interest for a given application.

The lighting system can advantageously be implemented and used in different scenarios and applications in which it could be desirable and practical to add or supplement the illumination light with non-visible light that can include, for example and without being limitative UV, far-red and/or IR portions of the electromagnetic spectrum. The system herein described is compatible with conventional light sources and could be added to the same to supplement the spectral content in predetermined portions of the electromagnetic spectrum, for example conventional light sources emitting in the visible portion of the natural light.

Extension Bar

Figure 4B:
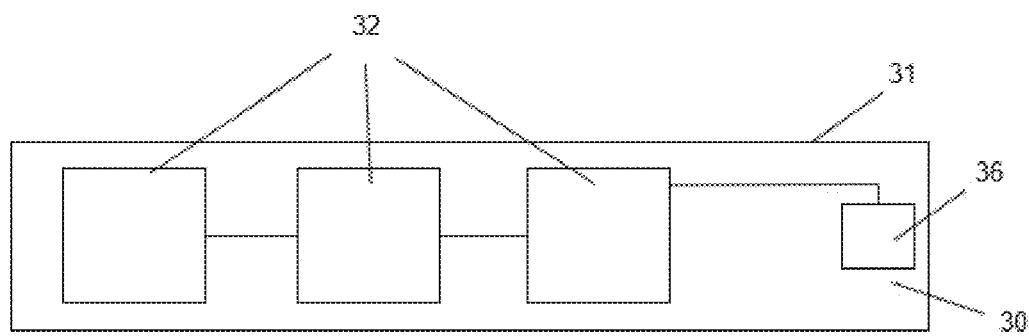
FIG. 4B shows an extension bar for supplementing a spectral content of the initial illumination originating from an illuminating lamp and irradiating a plant.

Now turning to FIG. 4B, the extension bar variant will now be described. In FIG. 4B, there is illustrated an extension bar 30 for supplementing a spectral content of an initial illumination originating from an illuminating lamp (not illustrated) and irradiating a plant, the illuminating lamp comprising a main controller. the extension bar comprising. The extension bar 30 includes an elongated body 31, one or more supplemental light emitters 32 mounted on the elongated body 31, each supplemental light emitter 32 being configured to emit non-visible light having an emitter spectrum in a non-visible range, and a local controller 36 provided on the elongated body 31 and being in communication with the main controller of the illuminating lamp. The local controller 36 is configured for determining a relative intensity between two emission spectra and controlling the supplemental light emitters 22 to adjust an intensity level of the emitter spectrum according to the relative intensity between said two emission spectra. In some embodiments, the each of the two emission spectra is associated with a corresponding one the supplemental light emitters. In other embodiments, one of the two emission spectra is associated with a corresponding one of said one or more supplemental light emitter and another one of the two emission spectra is associated with the initial illumination.

In some embodiments, the supplemental light emitters 32 of the extension bar 30 may comprise at least one far-red solid-state emitter, the emitter spectrum of each of said at least one far-red solid-state emitter comprising wavelengths between about 700 nm and about 860 nm. In some embodiments, the supplemental light emitters 32 of the extension bar 30 may comprise at least one infrared solid-state emitter, the emitter spectrum of each of said at least one infrared solid-state emitter comprising wavelengths above about 860 nm. In some embodiments, the supplemental light emitters 32 of the extension bar 30 may comprise at least one ultraviolet (UV) emitter, the emitter spectrum of each of said at least one solid-state emitter comprising wavelengths between about 10 nm and about 400 nm.

In some embodiments, the supplemental light emitters 32 are light emitting diodes. The supplemental light emitters 32 may be one of a semiconductor light emitting diode, a semiconductor laser diode, a vertical cavity surface emitting laser, an organic light-emitting diode or a polymer light-emitting diode.

In some embodiments, the supplemental light emitters 32 comprises a plurality of blocks of light emitting diodes. The supplemental light emitters 32 may be arranged in a uniform matrix configuration, the plurality of blocks of light emitting diodes comprising at least one of: a block of far-red light emitting diodes, a block of infrared light-emitting diodes and a block of ultraviolet light emitting diodes spaced apart along said elongated body. The supplemental light emitters 32 may be arranged in a mixed matrix configuration, each of the blocks of light emitting diodes comprising at least two of: a far-red light emitting diode, an infrared light-emitting diodes and an ultraviolet light emitting diodes spaced apart along said elongated body.

In some embodiments, the local controller 36 operates the one or more light-emitting diodes according to a Pulse Width Modulation scheme.

In some embodiments, the extension bar 30 may include a wired connection for connecting the extension bar and the illuminating lamp. The wired connection may carry control signals and supply electrical power to the extension bar 30.

In other embodiments, the extension bar 30 may include a wireless communication module for wirelessly receiving the control signals from the illuminating lamp and a local power supply provided on the elongated body.

Modular Illumination Assembly

Figure 4C:
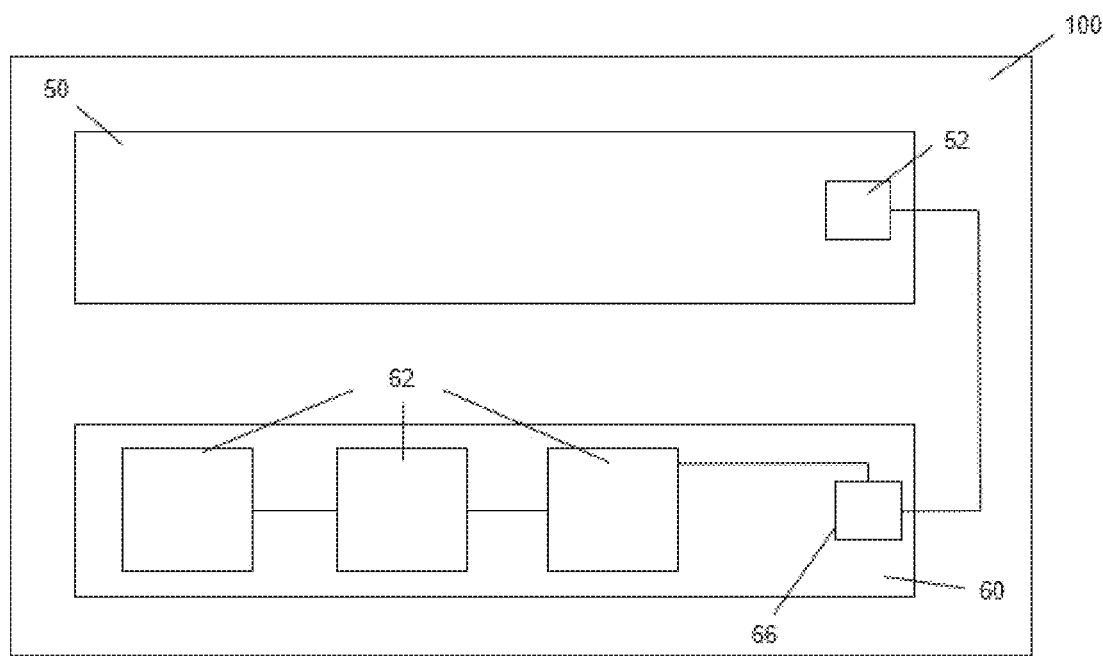
FIG. 4C illustrates a modular illumination assembly for irradiating a plant.

With reference to FIG. 4C, a modular illumination assembly 100 for irradiating a plant will now be described. The modular illumination assembly includes a visible illumination module 50 and a non-visible illumination module 60. The visible illumination module 50 includes a main controller 52. The visible illumination module 50 is configured to emit an initial illumination and irradiate a plant. The initial illumination typically has an initial spectrum in a visible range. The non-visible illumination module 60 is operatively connectable with the visible illumination module 50. The non-visible illumination module 60 includes one or more supplemental light emitters 62, each supplemental light emitter 62 being configured to emit non-visible light having an emitter spectrum in a non-visible range. The non-visible illumination module 60 also includes a local controller 66 in communication with the main controller 52 of the visible illumination module 50. The local controller 62 is configured for determining a relative intensity between two emission wavelengths and controlling said one or more supplemental light emitters to emit the non-visible light according to the relative intensity between two emission wavelengths. Each one of the visible illumination module 50 and the non-visible illumination module 60 may be selectively mounted, unmounted and/or replaced.

In some embodiments, each of the two emission wavelengths is associated with a corresponding one of the supplemental light emitters 62. In other embodiments, one of the two emission wavelengths is associated with a corresponding one of the supplemental light emitters 62 and another one of the two emission wavelengths is associated with the initial illumination.

In some embodiments, the supplemental light emitters 62 may comprise at least one far-red solid-state emitter, the emitter spectrum of each the far-red solid-state emitter comprising wavelengths between about 700 nm and about 860 nm. In some embodiments, the supplemental light emitters 62 may comprise at least one infrared solid-state emitter, the emitter spectrum of each of the infrared solid-state emitter comprising wavelengths above about 860 nm. In some embodiments, the supplemental light emitters 62 may comprise at least one ultraviolet (UV) emitter, the emitter spectrum of each of the solid-state emitter comprising wavelengths between about 10 nm and about 400 nm.

In some embodiments, the supplemental light emitters 62 may be light emitting diodes, a semiconductor light emitting diode, a semiconductor laser diode, a vertical cavity surface emitting laser, an organic light-emitting diode or a polymer light-emitting diode.

In some embodiments, the supplemental light emitters 62 comprises a plurality of blocks of light emitting diodes. The supplemental light emitters 62 may be arranged in a uniform matrix configuration, the plurality of blocks of light emitting diodes comprising at least one of: a block of far-red light emitting diodes, a block of infrared light-emitting diodes and a block of ultraviolet light emitting diodes. The supplemental light emitters 62 may be arranged in a mixed matrix configuration, each of the blocks of light emitting diodes comprising at least two of: a far-red light emitting diode, an infrared light-emitting diode and an ultraviolet light emitting diode.

In some embodiments, the local controller 66 operates the one or more light-emitting diodes according to a Pulse Width Modulation scheme.

In some embodiments, the modular illumination assembly 100 may include a wired connection 102 for connecting the non-visible illumination module 60 and the visible illumination module 50, The wired connection 102 may carry control signals and supply electrical power to the non-visible illumination module 60. In other embodiments, the non-visible illumination module 60 may include a wireless communication module for wirelessly receiving the control signals from the visible illumination module 50. The non-visible illumination module 60 may include a local power supply.

Determination of Ratios

Now turning to FIGS. 5 to 16, different scenarios implementing the methods and systems having been described will now be presented.

Figure 5:
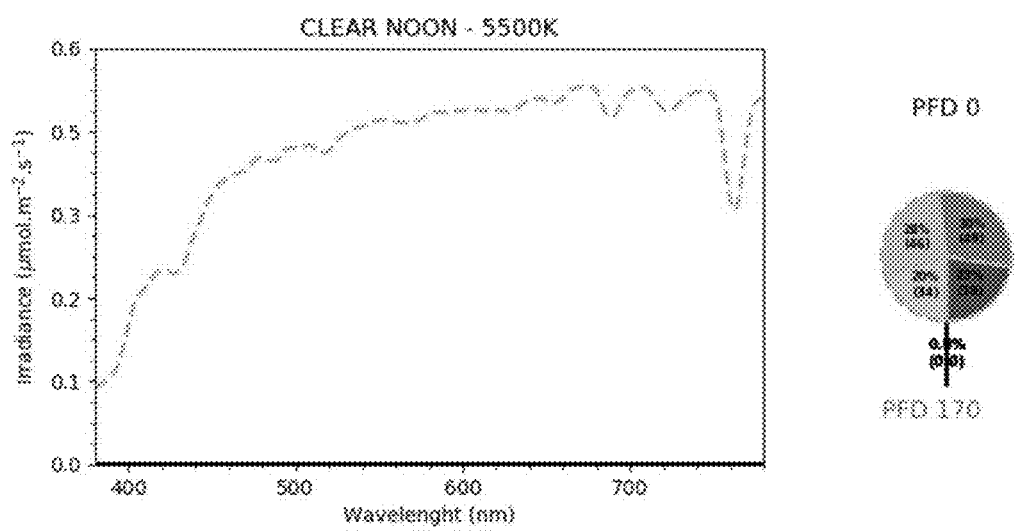
FIG. 5 illustrates the spectral profile of the Sun at noon, which corresponds to a color temperature of about 5500 K.
Figure 6:
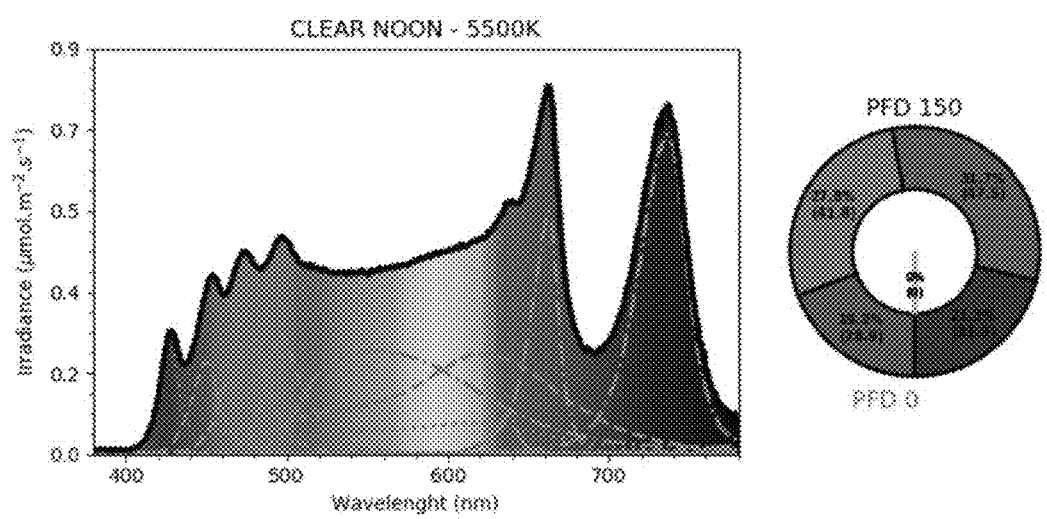
FIG. 6 shows a global illuminating output, combining the initial illumination from the illuminating lamp and the non-visible light provided by the supplemental light assembly or the extension bar, in accordance with one embodiment.
Figure 7:
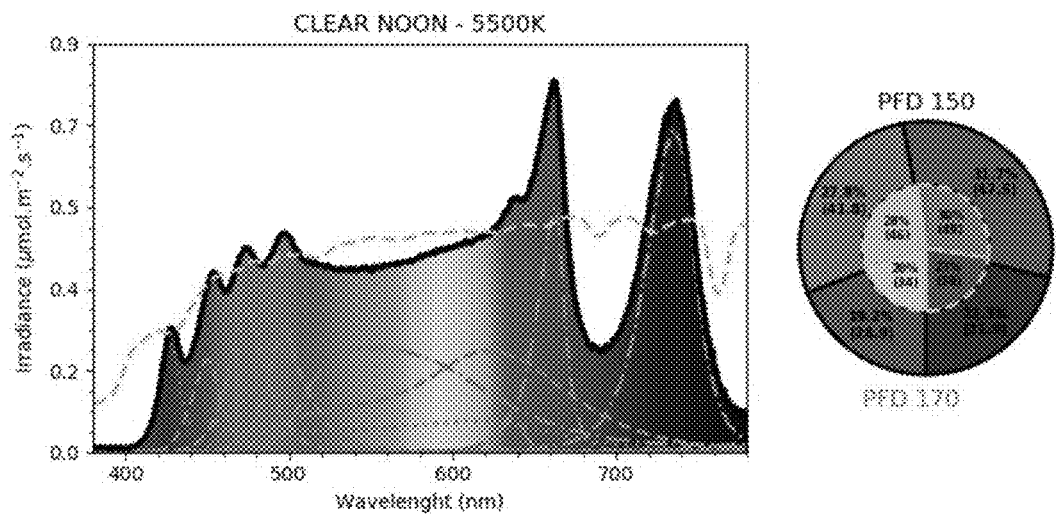
FIG. 7 illustrates the superimposition of FIGS. 5 and 6.

In FIGS. 5 to 7, a clear noon scenario is illustrated. FIG. 5 illustrates the spectral profile of the Sun at noon, which corresponds to a color temperature of about 5500 K. On the right, the proportions of each of the components of the spectral profile is illustrated. It will be noted that the spectral profile may be characterized by the relative intensity between two or more wavelengths or spectral bands. For example, the spectral profile may be characterized by a relative intensity between blue light and green light present in the spectral profile, a relative intensity between blue light and red light present in the spectral profile, a relative intensity between red light and far-red light present in the spectral profile, and/or any combinations thereof. The supplemental light emitters of the supplemental illumination assembly or the extension bar may be driven or controlled to obtain a supplemented light according to the relative intensity between two or more wavelengths or spectral bands. The global illuminating output, combining the initial illumination from the illuminating lamp and the non-visible light provided by the supplemental light assembly or the extension bar, is illustrated in FIG. 6. FIG. 6 illustrates that the supplemental light emitters may be operated such that the relative intensity between predetermined wavelengths or spectral bands is controlled to produce a supplemented light having a specific spectral profile, which may be particularly useful in the context of agriculture or horticulture applications. FIG. 7 illustrates the superimposition of FIGS. 5 and 6.

Figure 8:
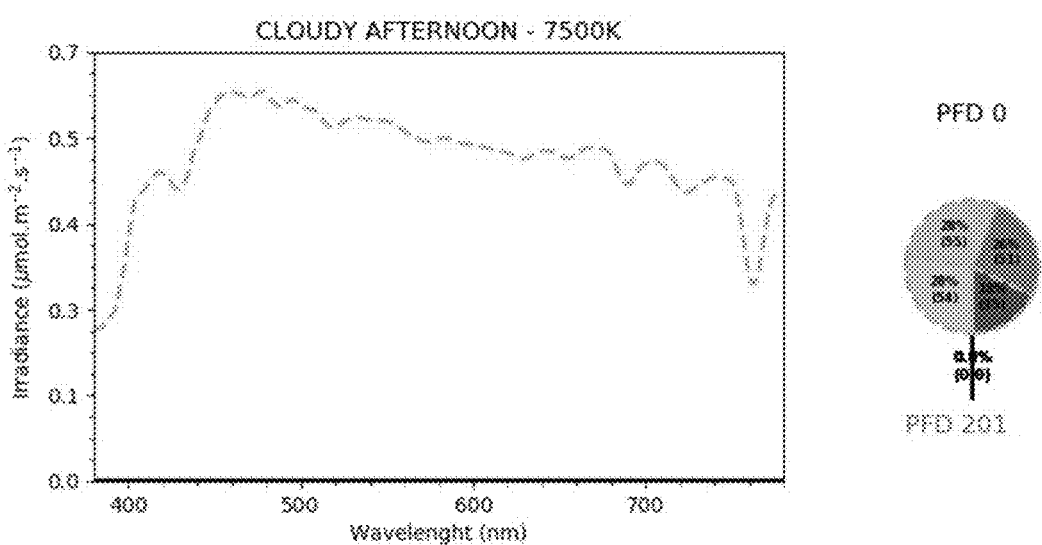
FIG. 8 FIG. 8 illustrates the spectral profile of the Sun during a cloudy afternoon, which corresponds to a color temperature of about 7500 K.
Figure 9:
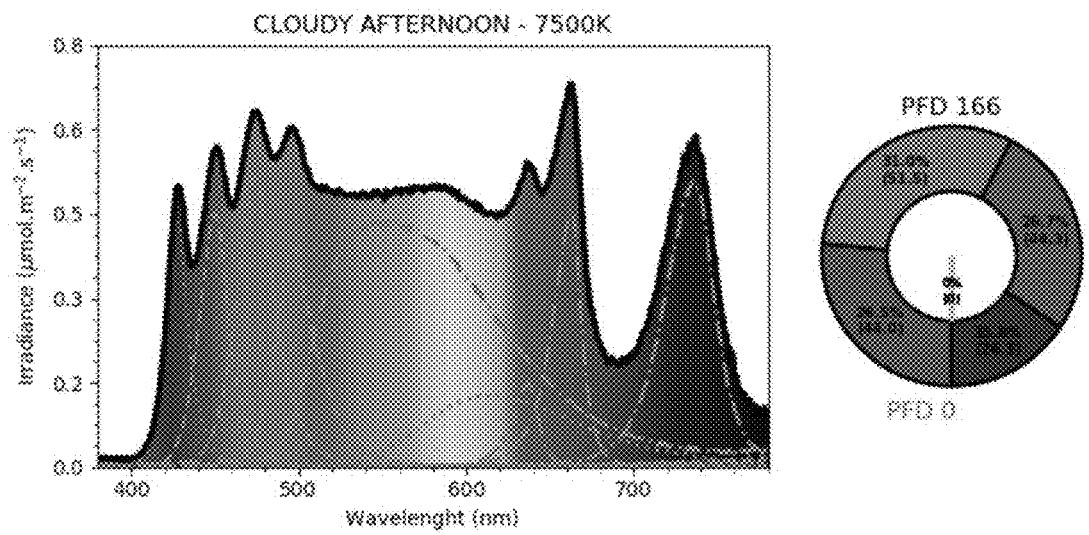
FIG. 9 shows a global illuminating output, combining the initial illumination from the illuminating lamp and the non-visible light provided by the supplemental light assembly or the extension bar, in accordance with one embodiment.
Figure 10:
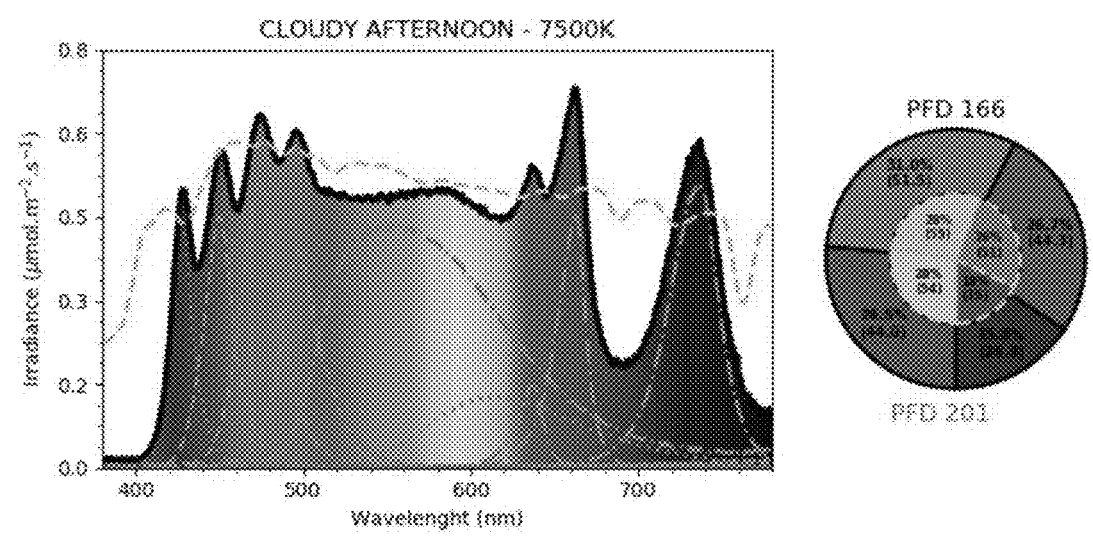
FIG. 10 illustrates the superimposition of FIGS. 8 and 9.

In FIGS. 8 to 10, a cloudy afternoon scenario is illustrated. FIG. 8 illustrates the spectral profile of the Sun during a cloudy afternoon, which corresponds to a color temperature of about 7500 K. On the right, the proportions of each of the components of the spectral profile is illustrated. On the right, the proportions of each of the components of the spectral profile is illustrated. It will be noted that the spectral profile may be characterized by the relative intensity between two or more wavelengths or spectral bands. For example, the spectral profile may be characterized by a relative intensity between blue light and green light present in the spectral profile, a relative intensity between blue light and red light present in the spectral profile, a relative intensity between red light and far-red light present in the spectral profile, and/or any combinations thereof. The supplemental light emitters of the supplemental illumination assembly or the extension bar may be driven or controlled to obtain a supplemented light according to the relative intensity between two or more wavelengths or spectral bands. The global illuminating output, combining the initial illumination from the illuminating lamp and the non-visible light provided by the supplemental light assembly or the extension bar, is illustrated in FIG. 9. FIG. 9 illustrates that the supplemental light emitters may be operated such that the relative intensity between predetermined wavelengths or spectral bands is controlled to produce a supplemented light having a specific spectral profile, which may be particularly useful in the context of agriculture or horticulture applications. FIG. 10 illustrates the superimposition of FIGS. 8 and 9.

Figure 11:
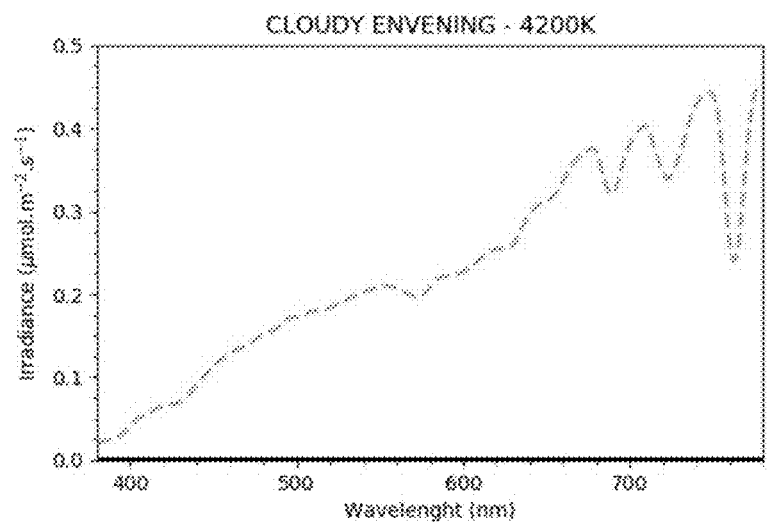
FIG. 11 illustrates the spectral profile of the Sun during a cloudy evening, which corresponds to a color temperature of about 4200 K.
Figure 11:
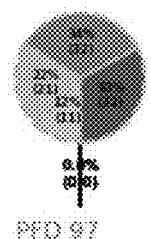
Figure 12:
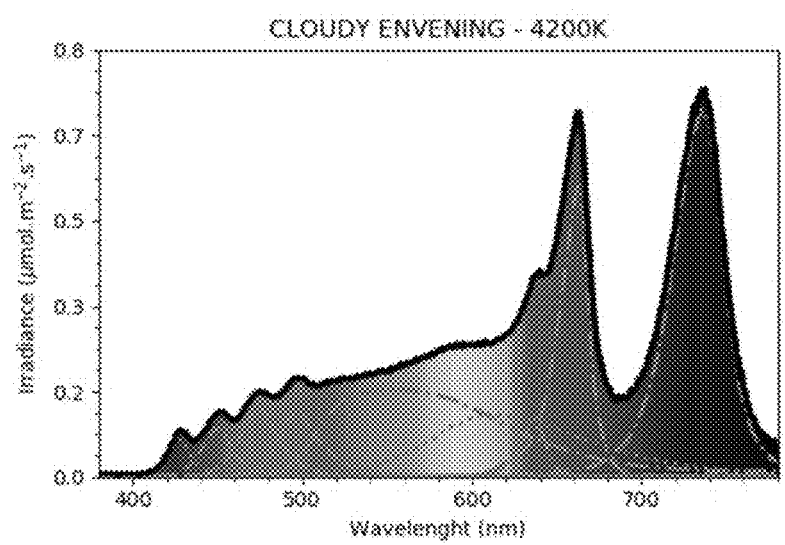
FIG. 12 shows a global illuminating output, combining the initial illumination from the illuminating lamp and the non-visible light provided by the supplemental light assembly or the extension bar, in accordance with one embodiment.
Figure 12:
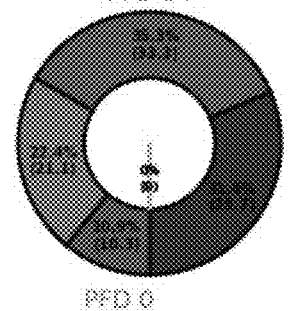
Figure 13:
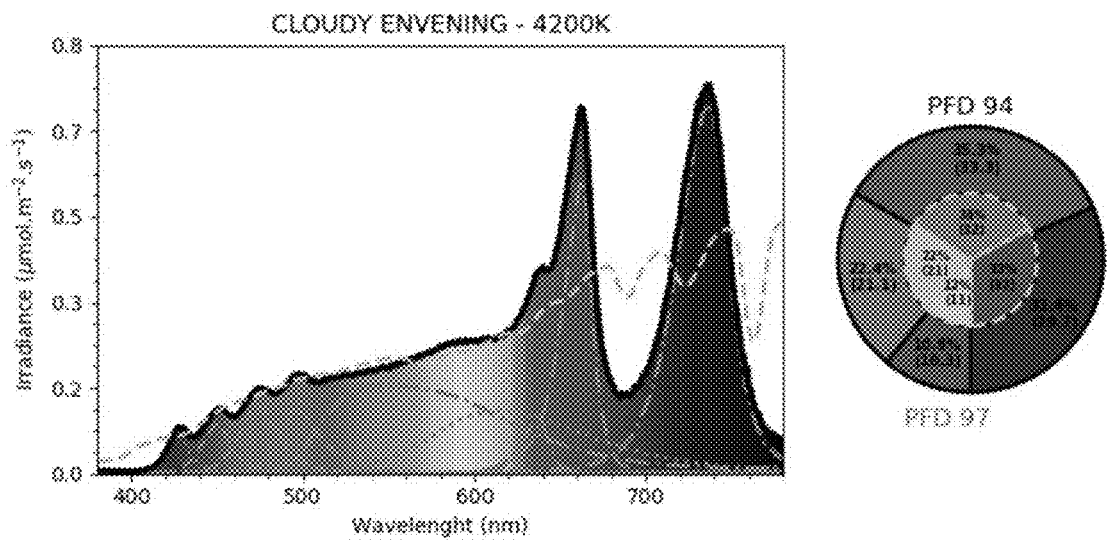
FIG. 13 illustrates the superimposition of FIGS. 11 and 12

In FIGS. 11 to 13, a cloudy evening scenario is illustrated. FIG. 11 illustrates the spectral profile of the Sun during a cloudy evening, which corresponds to a color temperature of about 4200 K. On the right, the proportions of each of the components of the spectral profile is illustrated. On the right, the proportions of each of the components of the spectral profile is illustrated. It will be noted that the spectral profile may be characterized by the relative intensity between two or more wavelengths or spectral bands. For example, the spectral profile may be characterized by a relative intensity between blue light and green light present in the spectral profile, a relative intensity between blue light and red light present in the spectral profile, a relative intensity between red light and far-red light present in the spectral profile, and/or any combinations thereof. The supplemental light emitters of the supplemental illumination assembly or the extension bar may be driven or controlled to obtain a supplemented light according to the relative intensity between two or more wavelengths or spectral bands. The global illuminating output, combining the initial illumination from the illuminating lamp and the non-visible light provided by the supplemental light assembly or the extension bar, is illustrated in FIG. 12. FIG. 12 illustrates that the supplemental light emitters may be operated such that the relative intensity between predetermined wavelengths or spectral bands is controlled to produce a supplemented light having a specific spectral profile, which may be particularly useful in the context of agriculture or horticulture applications. FIG. 13 illustrates the superimposition of FIGS. 11 and 12.

Figure 14:
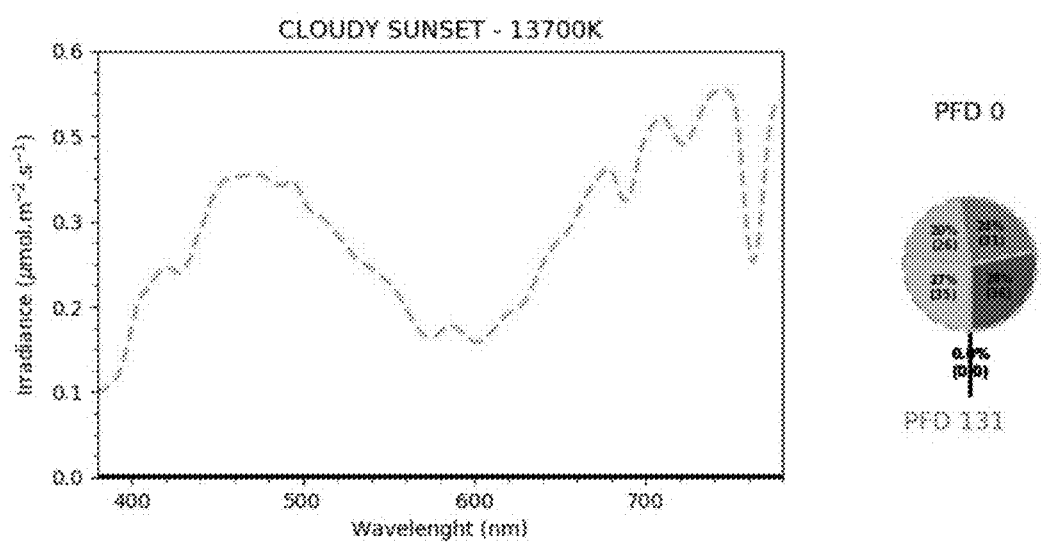
FIG. 14 illustrates the spectral profile of the Sun during a cloudy sunset, which corresponds to a color temperature of about 13,700 K
Figure 15:
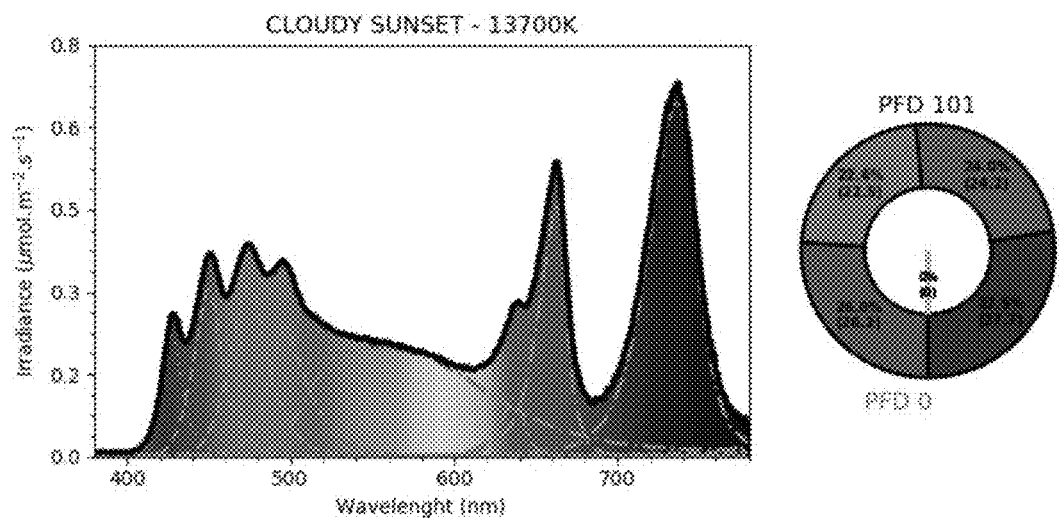
FIG. 15 shows a global illuminating output, combining the initial illumination from the illuminating lamp and the non-visible light provided by the supplemental light assembly or the extension bar, in accordance with one embodiment.
Figure 16:
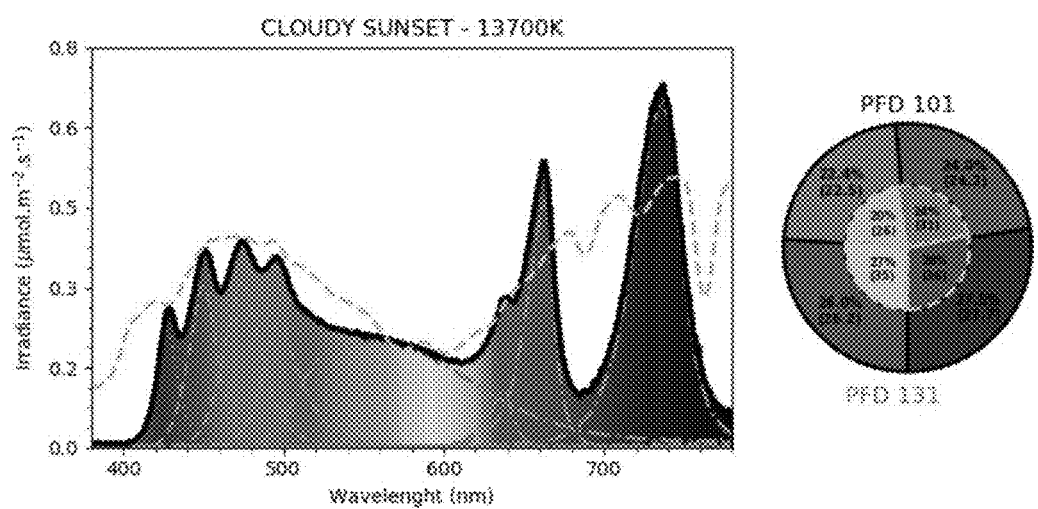
FIG. 16 illustrates the superimposition of FIGS. 14 and 15.

In FIGS. 14 to 16, a cloudy sunset scenario is illustrated. FIG. 14 illustrates the spectral profile of the Sun during a cloudy sunset, which corresponds to a color temperature of about 13,700 K. On the right, the proportions of each of the components of the spectral profile is illustrated. On the right, the proportions of each of the components of the spectral profile is illustrated. It will be noted that the spectral profile may be characterized by the relative intensity between two or more wavelengths or spectral bands. For example, the spectral profile may be characterized by a relative intensity between blue light and green light present in the spectral profile, a relative intensity between blue light and red light present in the spectral profile, a relative intensity between red light and far-red light present in the spectral profile, and/or any combinations thereof. The supplemental light emitters of the supplemental illumination assembly or the extension bar may be driven or controlled to obtain a supplemented light according to the relative intensity between two or more wavelengths or spectral bands. The global illuminating output, combining the initial illumination from the illuminating lamp and the non-visible light provided by the supplemental light assembly or the extension bar, is illustrated in FIG. 15. FIG. 15 illustrates that the supplemental light emitters may be operated such that the relative intensity between predetermined wavelengths or spectral bands is controlled to produce a supplemented light having a specific spectral profile, which may be particularly useful in the context of agriculture or horticulture applications. FIG. 16 illustrates the superimposition of FIGS. 14 and 15.

Example of an Application

Now that different embodiments of techniques, methods, systems and assemblies for supplementing the spectral content of an initial illumination have been described, an example of a potential application of the technology will now be presented. In agriculture, non-visible light can be useful for different reasons. For example, and without being limitative, the UV-C range can be used for cleaning and disinfecting the plants and the UV-A and UV-B ranges can be useful for the insects and to stimulate the work of the pollinating insects. As such, the technology described above can potentially be used to increase or enhance the speed and the quality of the flowering, clean and disinfect plants or flowers (e.g., for microorganisms suppression, such as and without being limitative, bacteria), facilitate or active certain chemical reactions in the plant (e.g., THC and cannabinoid in cannabis plant), facilitate the pollination by emitting wavelengths necessary for the bees and many others. In other words, combining or supplementing visible illumination with non-visible light can cause various effects on the plants and insects. As for the far-red and IR ranges, far-red range can be beneficial for the growth of the plants, the fruit coloration, to increase the vitamins (e.g. vitamin C), to increase the sugar level and increase the quality of the fruits and many others. As such, supplementing the illumination with far-red and IR illumination can have some benefits like, for example and without being limitative helping the plant in its generative phase, helping the production of fruits and helping the stretching and elongation of the plants.

The techniques presented in the current description may have some advantages for a grower. For example, and without being limitative, the grower can select and adapt the lighting conditions of the growing plants, by illuminating the plants with visible light in some instances and with a combination of visible and non-visible lights in others. The systems and assemblies provided herein allow a certain level of modularity by selectively mounting/demounting light emitters emitting in certain region of the electromagnetic spectrum, e.g., UV, far-red and/or IR. As such the technology that has been described can be used to the spectral content of an existing light source, based on a specific targeted application.

Several alternative embodiments and examples have been described and illustrated herein. The embodiments described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. The present examples and embodiments, therefore, are to be considered in all respects as illustrative and not restrictive. Accordingly, while specific embodiments have been illustrated and described, numerous modifications come to mind without significantly departing from the scope defined in the appended claims.

The invention claimed is:

1. A supplemental illumination assembly for supplementing a spectral content of an initial illumination originating from an illuminating lamp, the illuminating lamp comprising a main controller, the supplemental illumination assembly comprising:

an elongated body;
a plurality of supplemental light emitters mounted on the elongated body, each supplemental light emitter being configured to emit light having an emitter spectrum in a non-visible range; and
a local controller provided on the elongated body and configured to control the supplemental light emitters, the local controller being in communication with the main controller of the illuminating lamp to receive control signals therefrom.

2. The supplemental illumination assembly of claim 1, wherein said supplemental light emitters comprise at least one far-red solid-state emitter, the emitter spectrum of each of said at least one far-red solid-state emitter comprising wavelengths between about 700 nm and about 860 nm.

3. The supplemental illumination assembly of claim 1, wherein said supplemental light emitters comprise at least one infrared solid-state emitter, the emitter spectrum of each of said at least one infrared solid-state emitter comprising wavelengths above about 860 nm.

4. The supplemental illumination assembly of claim 1, wherein said supplemental light emitters comprise at least one ultraviolet (UV) emitter, the emitter spectrum of each of said at least one UV emitter comprising wavelengths between about 10 nm and about 400 nm.

5. The supplemental illumination assembly of claim 1, wherein said supplemental light emitters are light emitting diodes.

6. The supplemental illumination assembly of claim 1, wherein each of said supplemental light emitters is one of a semiconductor light emitting diode, a semiconductor laser diode, a vertical cavity surface emitting laser, an organic light-emitting diode or a polymer light-emitting diode.

7. The supplemental illumination assembly of claim 1, wherein said supplemental light emitters comprises a plurality of blocks of light emitting diodes.

8. The supplemental illumination assembly of claim 7, wherein said supplemental light emitters are arranged in a uniform matrix configuration, the plurality of blocks of light emitting diodes comprising at least one of a block of far-red light emitting diodes, a block of infrared light-emitting diodes and a block of ultraviolet light emitting diodes spaced apart along said elongated body.

9. The supplemental illumination assembly of claim 7, wherein said supplemental light emitters are arranged in a mixed matrix configuration, each of said plurality of blocks of light emitting diodes comprising at least two of a block of far-red light emitting diode, a block of infrared light-emitting diode and a block of ultraviolet light emitting diode spaced apart along said elongated body.

10. The supplemental illumination assembly of claim 1, wherein the local controller operates said supplemental light emitters according to a Pulse Width Modulation scheme.

11. The supplemental illumination assembly of claim 1, further comprising a wired connection for connecting said supplemental illumination assembly and the illuminating lamp, said wired connection carrying said control signals and supplying electrical power to the supplemental illumination assembly.

12. The supplemental illumination assembly of claim 1, further comprising:
a wireless communication module for wirelessly receiving the control signals from the illuminating lamp; and
a local power supply provided on the elongated body.

13. The supplemental illumination assembly of claim 1, wherein the elongated body comprises an extension bar connectable to the illuminating lamp.

14. A method for supplementing a spectral content of an initial illumination originating from an illuminating lamp, the illuminating lamp comprising a main controller, the method comprising:
providing a supplemental illumination assembly, the supplemental illumination assembly comprising:
an elongated body;
one or more supplemental light emitters mounted on the elongated body, each supplemental light emitter being configured to emit light having an emitter spectrum in a non-visible range; and
a local controller provided on the elongated body and configured to control the supplemental light emitters, the local controller being in communication with the main controller of the illuminating lamp to receive control signals therefrom; and
combining the light from each of said supplemental light emitters with the initial illumination.

15. The method of claim 14, wherein said one or more supplemental light emitters comprises at least one far-red solid-state emitter, the emitter spectrum of each of said at least one far-red solid-state emitter comprising wavelengths between about 700 nm and about 860 nm.

16. The method of claim 14, wherein said one or more supplemental light emitters comprises at least one infrared (IR) solid-state emitter, the emitter spectrum of each of said at least one IR solid-state emitter comprising wavelengths above about 860 nm.

17. The method of claim 14, wherein said one or more supplemental light emitters comprises at least one ultraviolet (UV) emitter, the emitter spectrum of each of said at least one UV emitter comprising wavelengths between about 10 nm and about 400 nm.

18. The method of claim 14, further comprising independently adjusting an intensity level of the light from each of said one or more supplemental light emitters.

19. The method of claim 14, further comprising controlling said one or more supplemental light emitters in view of a target spectrum of the combined light from said supplemental light emitters and said initial illumination.

* * * * *